US009668975B2

(12) United States Patent
Kuo et al.

(10) Patent No.: US 9,668,975 B2
(45) Date of Patent: Jun. 6, 2017

(54) METHOD OF PREPARING DRUG AGGLOMERATE

(71) Applicant: PharmaDax Inc., New Taipei (TW)

(72) Inventors: Pei-Chun Kuo, New Taipei (TW); Shih-Wei Huang, New Taipei (TW); Chiung-Fang Chang, New Taipei (TW)

(73) Assignee: PharmaDax Inc., New Taipei (TW)

( * ) Notice: Subject to any disclaimer, the term of this patent is extended or adjusted under 35 U.S.C. 154(b) by 0 days.

(21) Appl. No.: 14/881,171

(22) Filed: Oct. 13, 2015

(65) Prior Publication Data

US 2016/0101055 A1    Apr. 14, 2016

Related U.S. Application Data

(60) Provisional application No. 62/063,402, filed on Oct. 14, 2014.

(51) Int. Cl.
| | |
|---|---|
| *C08J 3/12* | (2006.01) |
| *A61K 9/16* | (2006.01) |
| *A61K 31/381* | (2006.01) |
| *A61K 9/20* | (2006.01) |
| *A61K 9/50* | (2006.01) |

(52) U.S. Cl.
CPC .......... *A61K 9/1688* (2013.01); *A61K 9/1617* (2013.01); *A61K 9/2081* (2013.01); *A61K 9/5073* (2013.01); *A61K 31/381* (2013.01); *C08J 3/12* (2013.01); *A61K 9/5042* (2013.01)

(58) Field of Classification Search
CPC ....................................................... C08J 3/12
See application file for complete search history.

(56) References Cited

U.S. PATENT DOCUMENTS

| | | |
|---|---|---|
| 5,508,276 A | 4/1996 | Anderson et al. |
| 6,531,490 B1 | 3/2003 | Horvath et al. |

FOREIGN PATENT DOCUMENTS

EP        0273658 B1    10/1990

OTHER PUBLICATIONS

Eva M. Ålander et al., "Characterization of paracetamol agglomerates by image analysis and strength measurement," Powder Technology, vol. 130, Issues 1-3, pp. 298-306, 2003.
Y. Kawashima et al., "An Experimental Study of the Kinetics of Spherical Agglomeration in a Stirred Vessel," Powder Technology, vol. 10, Issues 1-2, pp. 85-92, 1974.
Y. Kawashima et al., "Spherical Crystallization: Direct Spherical Agglomeration of Salicylic Acid Crystals During Crystallization," Science, vol. 216, pp. 1127-1128, Jun. 4, 1982.
Parthasarathi Keshavarao Kulkarni et al., "Spherical Agglomeration of Naproxan by Solvent Change Method," Stamford Journal of Pharmaceutical Sciences, vol. 4, No. 1, pp. 1-8, 2011.

(Continued)

*Primary Examiner* — Carlos Azpuru
(74) *Attorney, Agent, or Firm* — CKC & Partners Co., Ltd.

(57) ABSTRACT

A method of preparing drug agglomerates includes adding a drug powder to a first solvent to form a first solution, adding a second solvent to the first solution to form a second solution. The drug powder undergoes nucleation to form drug agglomerates. The drug agglomerates are isolated from the second solution.

9 Claims, 4 Drawing Sheets

(56) References Cited

OTHER PUBLICATIONS

Nitan Bharti et al., "Spherical Crystallization: A Novel Drug Delivery Approach," Asian Journal of Biomedical and Pharmaceutical Sciences, vol. 3, No. 18, pp. 10-16, 2013.
Damineni Saritha et al., "Improved dissolution and micromeritic properties of naproxen from spherical agglomerates: preparation, in vitro and in vivo characterization," Brazilian Journal of Pharmaceutical Sciences, vol. 48, No. 4, Oct./Dec. 2012.
Hsiang-yu Hsieh, "Spherical Crystallization for Lean Solid-Dose Manufacturing by Initial Solvent Screening : The Study of Phenylbutazone," Graduate Institute of Materials Science & Engineering National Central University, Jun. 2008.

METHOD OF PREPARING DRUG AGGLOMERATE

RELATED APPLICATIONS

This application claims priority to U.S. Provisional Application Ser. No. 62/063,402, filed Oct. 14, 2014, which is herein incorporated by reference.

BACKGROUND

Field of Invention

The instant disclosure relates to a method of preparing drug. More particularly, the instant disclosure relates a method of preparing drug agglomerate.

Description of Related Art

In the pharmaceutical industry, particle characterization of powder materials has become one of the crucial aspects in drug product development and it should be critically controlled within the formulating processes especially for solid oral dosage forms. The size distribution and shape of the particles can affect bulk properties and processability, thus during the formulating processes such as blending, tabletting and pellet coating it is required to have the particles in similar size at first. In addition, the particle size distribution of the drug substance may also have significant effects on final drug product performance (e.g., dissolution, bioavailability, content uniformity, stability, etc.)

The problems result from poor particle characterization can be solved by granulation. Granulation is a method to obtain larger particles in homogenized size distribution that can be used to facilitate formulation. In the practice, two types of granulation technologies are employed, namely, wet granulation and dry granulation. In wet granulation, granules are formed by the addition of a granulation liquid onto a powder bed which is under the influence of an impeller (in a high shear granulator or a twin screw granulator) or air (in a fluidized bed granulator). The agitation resulting in the system along with the wetting of the components within the formulation results in the aggregation of the primary powder particles to produce wet granules. The granulation liquid contains solvent which must be volatile so that it can be removed by drying. Conventional liquid include water, ethanol and isopropanol either alone or in combination. The dry granulation process is used to form granules without using a liquid solution because the product granulated may be sensitive to moisture and heat. Forming granules without moisture requires compacting and densifying the powders. In this process the primary powder particles are aggregated under high pressure. Either a large tablet (known as a "slug") is produced in a complicate tablet press or the powder is squeezed between two rollers to produce a sheet of material (roller compactor). In both cases these intermediate products are then broken and sieved to desired size. However, if the drug is physical or chemical unstable, these techniques should not be adopted because the moisture and heat may accelerate the degradation of drug (in wet granulation) or the high compression pressure may force the drug to degradation (in dry granulation). By the way, theses granulation methods both need special equipment.

A fixed size drug loaded bead is another way to control the particle size. It is achieved by spraying a drug contained solution/suspension onto fixed size inert beads in a fluidized bed or in a centrifugal-fluid type granulator. However, it usually takes a prolonged time to load the drug onto the beads, especially for a large dosing quantity. Further, it also takes longer to apply a release rate controlling layer over such drug loaded bead.

In addition to the abovementioned methods, modifying the particle characterization of raw materials at source is another way to improve or provide additional functionality of excipients. Several pharmaceutical excipient suppliers can provide different grades of product that are suitable for various purposes. However, regarding to the drug substance, the choice is limited. That may be due to the inherent property of the drug substances or other cost considerations.

Spherical crystallization is a process of obtaining larger particles in spherical shape, by which crystallization and agglomeration can be carried out simultaneously and which can be utilized for improvement of flowability and compatibility of crystalline drugs (*Powder Technol.* 130, 2003, 298-306). Depending on the target particle characteristics, different techniques have been used for producing spherical crystals, for example, spherical agglomeration, ammonia diffusion method, emulsion solvent diffusion and neutralization method.

In 1974, Kawashima and Capes introduced the concept of obtaining larger particles by agglomeration during the crystallization step. Silica sand is dispersed in agitated carbon tetrachloride and agglomerated with calcium chloride aqueous solution. This process was used as a model system (*Powder Technol.* 10, 1974, 85-92). Later, Kawashima further disclosed a method to obtain a size enlargement of particles during the crystallization step by controlling crystal agglomeration with controlled properties (*Science* 4 Jun. 1982, 1127-1128). His method employed three solvents: one was the drug dissolution medium, i.e., good solvent; another was a medium which partially dissolves the drug and is moist, i.e., bridging liquid; and the last one was immiscible with the drug substance, i e. poor solvent. The drug particles were first dissolved in good solvent, followed by re-crystallization when poured into poor solvent, and then agglomeration after bridging liquid was added. However, it is difficult to fully control the crystal property of the drug during dissolution-recrystallization procedure because the drug may not form an ideal shape or a desirable size which highly depends on drug nature and process parameters. In addition, whether the spherical agglomerates disclosed in those previous studies can be coated under pharmaceutical mass scale is uncertain.

SUMMARY

The instant disclosure provides a method of preparing drug agglomerates. The spherical agglomerates produced thereby contains drug in high concentration. The drug may be crystallized or non-crystallized. The size of the agglomerate ranges between 0.1 and 2.0 mm, preferably between 0.1 and 1.5 mm, or 0.1 and 1.0 mm. The agglomerates can selectively be coated by other coating.

According some embodiments of the instant disclosure, a method of preparing drug agglomerates includes adding a drug powder to a first solvent to form a first solution, adding a second solvent to the first solution to form a second solution. The drug powder undergoes nucleation to form drug agglomerates. The drug agglomerates are isolated from the second solution.

According some embodiments of the instant disclosure, an oral drug composition includes agglomerates whose diameter ranges between 0.1 and 2.0 mm and drug concentration higher than 95% (w/w).

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
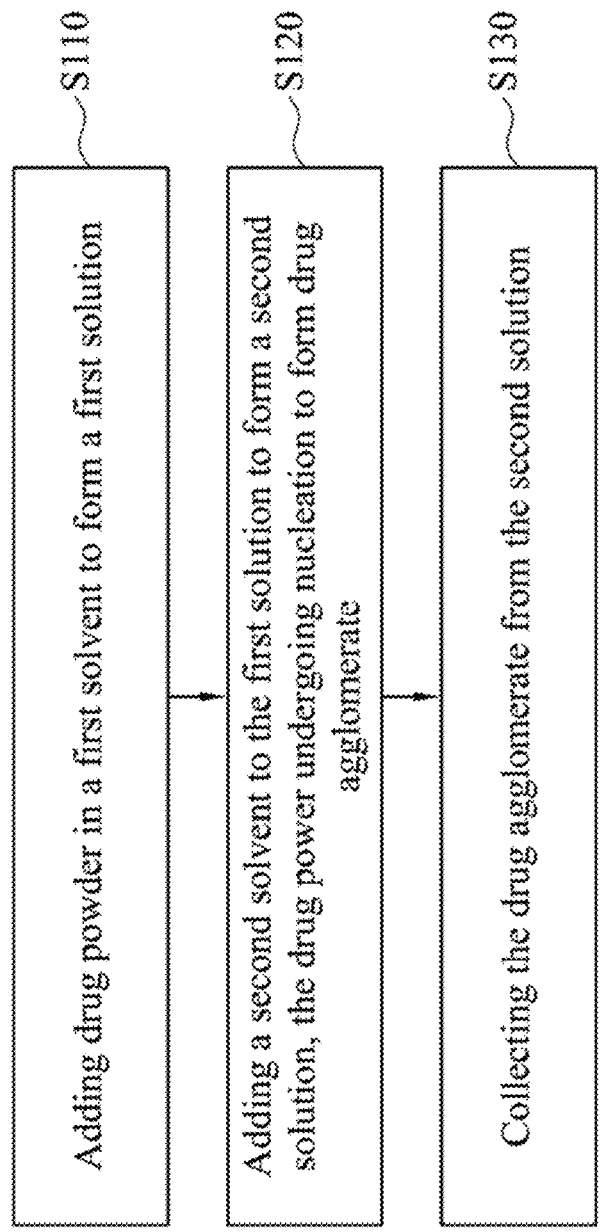
FIG. 1 is a flow chart illustrating a method of preparing drug agglomerates in accordance with an embodiment of the instant disclosure.

Reference will now be made in detail to the present embodiments of the invention, examples of which are illustrated in the accompanying drawings. Wherever possible, the same reference numbers are used in the drawings and the description to refer to the same or like parts.

The term "drug" means a substance used in the treatment, cure, or prevention of disease or used to otherwise enhance physical or mental well-being. The drug can be in the form of a single enantiomer, mixture of stereoisomers, free base or the pharmaceutical acceptable salt thereof. The preferable drug for the instant disclosure is for oral administration. The drug includes but not limited to those have poor stability, susceptible to gastrointestinal environment, need to be formulated in a modified release dosage form and large administrated quantity (low potency). The drug of the instant disclosure is an acid susceptible drug or the drug has a daily dose larger than 300 mg. Proton pump inhibitor, such as omeprazole, esomeprazole, lansoprazole, dexlansoprazole, pantoprazole, rabeprazole and ilaprazole, are some examples of the preferable acid susceptible drug in the instant disclosure. However, other acid susceptible drugs are also applicable.

The term "oral dosage form" means a dosage form that is delivered through mouth and can be but not limited to tablet, capsule, granule, powder, buccal film, sublingual film, oral paste, suspension, emulsion or syrup.

The term "excipient" means a pharmaceutically acceptable inactive substance for the purpose of bulking-up formulations that contain drug ingredients. It may be but not limited to binder, disintegrant, filler, film former, flavor, colorant, lubricant, glidant, sorbent, preservative, release rate controller or sweetener.

The term "modified release dosage form" means a dosage form that alters the timing and/or the rate of release of the drug substance. A modified-release dosage form is a formulation in which the drug-release characteristics of time course and/or location are chosen to accomplish therapeutic or convenience objectives not offered by a conventional dosage form such as a solution or an immediate release dosage form. Modified release dosage form includes both delayed and extended release drug products. The delayed release product is a formulation that releases a discrete portion or portions of drug at a time other than promptly after administration. The extended release product is formulated to make the drug available over an extended period after ingestion. The extended release product allows a reduction in dosing frequency compared to a drug presented as a conventional dosage form.

The term "release rate controlling material" means a material that regulates the drug release profile. It is, but not limited to, a material that does not dissolve in acid or basic condition, a material that does not dissolve or slowly dissolve when in contact with water, a material that swells when in contact with water to trap the drug from release, or a material that forms a gel when in contact with water. A gel material, an enteric material, or a non-erosion/non-dissolve material is a preferable release rate controlling material of the instant disclosure. It includes, for example, polyvinyl alcohol, sodium polyacrylate, hydroxypropyl methylcellulose, hydroxypropylcellulose, hydroxyethylcellulose, methylcellulose, carboxymethylcellulose, carboxymethyl hydroxyethylcellulose, carbomer, sodium carboxymethylcellulose, polyvinylpyrrolidone, methyl acrylate-methacrylic acid copolymers, cellulose acetate succinate, hydroxy propyl methyl cellulose phthalate, hydroxy propyl methyl cellulose acetate succinate, polyvinyl acetate phthalate, methyl methacrylate-methacrylic acid copolymers, sodium alginate, or ethylcellulose.

The term "enteric material" means a material that is stable at acidic pH than basic pH environment. For example, enteric material does not dissolve in the acidic juices of the stomach (pH ~3), but it dissolve in the alkaline (pH 7-9) environment in the small intestine. It includes but not limited to fatty acids, waxes, shellac, plastics, plant fibers and polymers.

The term "substantially pure" means the purity is at least 95% as measured by suitable analytical equipment.

The term "solvent" means water or organic solvent, wherein the organic solvent belongs to Class 2 solvents or Class 3 solvents listed in ICH Q3C Guideline which includes but not limited to $C_5$-$C_8$ alkanes, arenes, halogenoalkanes, alcohols, ketones, ethers, esters, nitriles, or amines.

The solubility is defined as that in the USP and NF Articles, i.e., "practically insoluble" means more than 10,000 parts of solvent needed for 1 part solute, "very slightly soluble" means 1,000-10,000 parts of solvent needed for 1 part solute, "slightly soluble" means 100-1000 parts of solvent needed for 1 part solute, "sparingly soluble" means 30-100 parts of solvent needed for 1 part solute, "soluble" means 10-30 parts of solvent needed for 1 part solute, "freely soluble" means 1-10 parts of solvent needs for 1 part solute, "very soluble" means less than 1 part of solvent needed for 1 part solute.

The instant disclosure provides drug agglomerates in spherical shape. The spherical shape is not limited to a regular sphere but includes irregular ball-like shape. The spherical drug agglomerates are obtained by spherical agglomeration of drug particles. The spherical drug agglomerates have an mean particle size of about 0.05 mm to 2 mm, preferably, about 0.1 mm to 1.5 mm, and more preferably, about 0.1 mm to 1.0 mm. The spherical drug agglomerates are substantially purely consisted of the drug.

As shown in FIG. 1, the instant disclosure provides a method of preparing spherical drug agglomerates including step S110 adding drug particles to a first solvent and allowing suspension. Next, in step S120 a second solvent is added to agglomerate the drug particles such that the drug agglomerates has a smoother contour. Then, in step S130, the drug agglomerates are collected. Optionally, the drug agglomerates may undergo drying process to remove excess solvent. An initial dissolution-recrystallization step of drug is omitted, and the agglomerates grow from a pre-determined particle size of the crude materials, and thus, the agglomerates are well controlled in a narrower size.

In another aspect, the instant disclosure provides a method to obtain spherical drug agglomerates including dissolving drug particles in a good solvent to form a near saturated solution. Subsequently, the saturated solution is mixed with a first solvent to precipitate drug crystals. Then, a second solvent is added to agglomerate the drug crystals. Following that, the agglomerates undergo spheronizing to produce spherical drug agglomerates. Afterwards, the spherical drug agglomerates are collected. The drug agglomerates may undergo drying process to remove excess solvent.

Step S110 and S120 are conducted under an agitation condition. In addition, the steps of dissolving the drug particles in the good solvent to form a saturated solution, mixing the saturated solution with the first solvent such that the drug particles undergo crystallization and then precipitate, and adding a second solvent to agglomerate the drug crystal are also under an agitation condition. The smoothing process is conducted under machine agitation, wherein the drug agglomerates are spheronized by the method of agitation to form ball-like agglomerates. The agitation can be carried out by a paddle apparatus. However, other suitable agitation apparatus may also be used. To enhance the efficiency of spheronization, it is better to have a number of baffles placed inside the reaction tank. The drug agglomerates are separated from the solvent by any suitable method, and a drying procedure may follow.

Compared to the second solvent, drug has lower solubility in the first solvent More specifically, the drug is nearly insoluble in the first solvent (less than 0.0001 g drug/g solvent). After dissolving the drug particles in the good solvent to form the saturated solution, the saturated solution is mixed with the first solvent and the drug crystals precipitate.

The good solvent is immiscible to the first solvent. Furthermore, the good solvent has a relatively higher solubility of the drug than the first solvent. More specifically, the drug is very soluble to soluble in the good solvent (that is more than 0.03 g drug/g solvent).

The first solvent may be, for example, $C_5$-$C_8$ alkane (e.g., pentane and heptane), arene (e.g., toluene and xylene), ethyl acetate, N,N-dimethylaniline and methyl ethyl ketone. The good solvent of the present invention, for example, includes but not limited to water, methanol, ethanol, isopropyl alcohol, n-butanol, acetonitrile, acetone, tetrahydrofuran, chloroform, 1,4-dioxane and dimethylformamide.

The second solvent is immiscible to the first solvent. In addition, the second solvent has a sparingly solubility to very slightly solubility to the drug (0.0001-0.03 g drug/g solvent). The second solvent is added in an amount to facilitate agglomerate the drug particles/crystals in the formation of larger size particles. In addition, in step S110, the first solvent can be pre-mixed with a portion of the second solvent before drug is added to the solution so as to facilitate drug dispersion within the first solvent and improve agglomeration efficiency. The second solvent of the instant disclosure includes but not limited to acetonitrile, methanol, ethanol, water, dimethylformamide or the mixture thereof. The selection of the second solvent depends on the first solvent and the drug property.

The second solvent is added gradually into the first solvent. However, a prolonged adding period may result in a wider size distribution of the agglomerates. It is found that the size and distribution of the spherical agglomerate can be efficiently controlled by reducing the second solvent droplet size. A conventional spray gun which provides a small size droplet, e.g., from about 0.1 mm to about 1.0 mm, and a wide spray zone is used, especially for a large production batch. However, other methods, e.g., drop by drop adding the second solvent to the first solvent or directly injecting the second solvent into the first solvent is also applicable.

The solvent used in forming the drug agglomerates depends on the property of the drug. For example, when using duloxetine hydrochloride as a drug model to obtain a spherical duloxetine particle, the first solvent may be heptane and the second solvent may be acetonitrile.

According to some embodiments of the instant disclosure, the mixture of good solvent and first solvent has a ratio of about 1:5 to 1:35 (v/v). The ratio of second solvent to first solvent (or good solvent plus first solvent) is from 1:20 to 1:70 (v/v).

The drug agglomerates produced thereby can undergo further processing. For example, the spherical agglomerates can be coated by a functional coat. The functional coat provides an additional feature, for example, regulating the drug release profile, improving stability, enhancing process feasibility or shielding property. The functional coat may be a coat that provides acid/base resistance, taste/odor masking, light/humidity protection or modified release profile.

The size and density of the drug agglomerates primarily depend on the particle size and shape of the crude material. A smaller crude material can result in smaller and smoother spherical agglomerate. For example, to obtain spherical agglomerates having a diameter of about 1.0 mm, a crude material having particle size of about 0.1 mm or less is preferable to be used as the starting material. For example, a drug particle having particle size $d_{90}$ less than 0.05 mm may be a starting material. Alternatively, a micronized drug particle having particle size $d_{90}$ less than 0.01 mm may also be used, and it has a better capacity to form a desirable spherical agglomerate size (i.e., about 0.1 mm to 1.0 mm) which benefits subsequent coating or tablet process. In addition, other parameters such as the selection of solvent system, drug concentration, volume ratios of liquids, agitation rate, liquid feeding method, processing temperature and the reaction time will also affect the property of the spherical agglomerates.

The following examples used duloxetine hydrochloride (duloxetine HCl) as a drug model to prepare the drug agglomerates. Duloxetine, a serotonin and norepinephrine reuptake inhibitor (SNRI), is first disclosed in European Patent No. 273658. Duloxetine is used in major depressive disorder (MDD), generalized anxiety disorder (GAD), diabetic peripheral neuropathic pain (DPNP) and fibromyalgia. It is used as a salt form, duloxetine hydrochloride, in the product and is currently marketed by Eli Lilly under the brand name Cymbalta® in the US. According to European Patent No. 273658, the duloxetine hydrochloride particle is synthesized from its needle-like crystals which need further processing to be formulated into a pharmaceutical product. According to the U.S. Pat. No. 5,508,276, it suggests to mill or to reduce the particle size of the duloxetine to less than 50 µm before coating the particle onto the loading beads through a powder coating process. Alternatively, the duloxetine particles dissolve or suspend in a solution and then is sprayed the solution onto the beads. Because the limitation of its crystal characteristics, currently commercial duloxetine products use the same formulation process as Cymbalta®. That is, a thin layer of duloxetine is applied on an inert core bead. However, the process is length and the production cost is higher.

The particle size distribution of the duloxetine HCl crude material in Examples 1-4 and 8-9 was about $d_{90}=7.9$ um, $d_{50}=43.6$ um and $d_{90}=119.5$ um. The particle size distribution of the duloxetine HCl crude material in Example 10 and 13 was about $d_{10}=0.6$ um, $d_{50}=1.8$ um and $d_{90}=5.2$ um.

Example 1

2.0 g of duloxetine HCl was suspended in 300 mL heptane at 20° C. under agitation (paddle, 400 rpm). 7 mL of acetonitrile was added gradually by dropping to the suspension. The system was left for 220 min to reach equilibrium (which refers to formation of constant size and smooth surface agglomerates) and product was then filtered off and dried at 40° C. for 20 hours. 1.8 g resulting agglomerates were obtained and had a spherical shape, and the mean particle size ranged from 1.0 mm to 1.8 mm. The average crushing strength of those agglomerates was about 230.7 g/bead. The method for crushing strength test was similar as those described in *Braz. J. Pharm. Sci. Vol.* 48 No. 4 October/December 2012, 667-676 or in *Asian Journal of Biomedical and Pharmaceutical Sciences* 3(18) 2013, 10-16. The DSC diagram of the drug product showed a peak at 173.8° C. that was similar as the starting material and the TGA profile showed no solvent was incorporated in the duloxetine agglomerates.

Example 2

9.0 g of duloxetine HCl was suspended in 300 mL heptane at 20° C. under agitation (paddle, 400 rpm). 6.6 mL of second solvent (acetonitrile: 95% ethanol=19:1) was added gradually to the suspension. The system was left for 200 min to reach equilibrium, and product was then filtered off and dried at 50° C. for 13 hours. 1.8 g resulting agglomerates were obtained and had a spherical shape, and the mean particle size ranged from 0.8 mm to 1.2 mm. The average crushing strength of those agglomerates was about 200 g/bead. The density was about 200 g/bead.

Example 3

9.0 g of duloxetine HCl was suspended in 300 mL heptane at 20° C. under agitation (paddle, 1000 rpm). 11 mL of acetonitrile was added gradually to the suspension. The system was left for 60 min to reach equilibrium and product was then filtered off and dried at 50° C. for 11 hours. 8.7 g resulting agglomerates were obtained and had a spherical shape, and the mean particle size ranged from 0.3 mm to 0.7 mm. The density was about 0.88 g/cm$^3$.

Example 4

20.0 g of duloxetine HCl was suspended in 300 mL heptane at 20° C. under agitation (paddle, 400 rpm). 15 mL of acetonitrile was added gradually to the suspension. The system was left for 210 min to reach equilibrium and product was then filtered off and dried at 50° C. for 12 hours. 19.6 g resulting agglomerates were obtained and had a spherical shape, and the mean particle size ranged from 0.8 mm to 1.0 mm. The agglomerate density was about 0.77 g/cm$^3$.

Example 5

The spherical duloxetine agglomerates for further enteric coating process were obtained by the procedure described in Example 4. The spherical duloxetine agglomerates were sieved by #60 mesh sieve. A coating solution, acting as a sealing layer, containing 22.5 g of HPMC 606, 45.0 g of sucrose, and 67.5 g of micro talc dissolved in 764.9 g of purified water was prepared, 300.0 g of the sieved spherical duloxetine agglomerates were placed in a fluidized bed and the coating solution was sprayed onto those particles. After the coating, the weight gain was about 30.7% and LOD was about 1.2%. The products then underwent the enteric layer coating procedure. 300.0 g of the coated agglomerates were further coated by an enteric layer coating solution, which contains 19.0 g of HPMCAS AS-LF 2.9 g of triethyl citrate and 8.1 g of stearic acid within 711.2 g of 95% ethanol. After this coating procedure the enteric polymer coated duloxetine pellets were formed and the weight gain was about 7.0% and LOD was about 1.2%. Each pellet contained about 71.5% w/w of duloxetine HCl.

TABLE 1

| Coating Condition | |
| --- | --- |
| Seal Layer | |
| Inlet Temperature (° C.) | 65-75 |
| Product Temperature (° C.) | 39-49 |
| Spray Air (bar) | 0.8-1.0 |
| Process Air (bar) | 0.2-0.4 |
| Spray Rate (g/min) | 5-9 |
| Enteric Layer | |
| Inlet Temperature (° C.) | 56-66 |
| Product Temperature (° C.) | 41-50 |
| Spray Air (bar) | 1.0-1.2 |
| Process Air (bar) | 0.4-0.5 |
| Spray Rate (g/min) | 6-8 |

Example 6

Dissolution Test of Enteric Polymer Coated Duloxetine Pellets

The coated duloxetine pellets obtained from Example 5 were assayed for dissolution test in Type I dissolution apparatus according to the U.S. Pharmacopoeia by a change buffer method (0.1N HCl for 2 hours then change to pH 6.8 PBS). A number of coated duloxetine pellets equivalent to 30 mg of duloxetine free base were packed into a #3 capsule for the test. The result is shown in Table 2.

TABLE 2

| 0.1N HCl 1000 mL; 200 rpm; 37° C. | |
| --- | --- |
| Time (min) | Release (%) |
| 60 | 0.55 |
| 120 | 6.76 |
| Change to pH 6.8 PBS 1000 mL; 100 rpm; 37° C. | |
| 145 | 31.58 |
| 160 | 46.54 |
| 175 | 53.84 |
| 190 | 58.31 |
| 205 | 63.27 |

Example 7

Dissolution Test of Spherical Duloxetine Agglomerates

The spherical duloxetine agglomerates obtained from Example 1 and 2 were assayed for dissolution test in a Type I dissolution apparatus according to the U.S. Pharmacopoeia under the condition of pH 6.8 PBS 500 mL; basket 100 rpm; 37° C. The duloxetine crude material was used as a comparison. According to Table 3, the result shows that the drug release profile of spherical agglomerates was similar to the crude material.

TABLE 3

| | Duloxetine Release (%) | | |
|---|---|---|---|
| Time (min) | Example 1 | Example 2 | Crude |
| 3 | 84.8 | 76.6 | 89.3 |
| 6 | 97.7 | 90.1 | 95.8 |
| 9 | 100.9 | 95.4 | 97.5 |
| 12 | 101.9 | 97.6 | 98.4 |
| 15 | 102.2 | 98.8 | 98.8 |
| 18 | 102.5 | 99.5 | 99.1 |
| 21 | 102.5 | 100.0 | 99.4 |
| 30 | 102.7 | 100.9 | 99.9 |
| 60 | 102.5 | 101.3 | 100.9 |

Example 8

2.0 g of duloxetine HCl was suspended in 300 mL heptane at 20° C. under agitation (paddle, 400 rpm). 0.8 mL of purified water was added gradually to the suspension. The system was left for 360 min to reach equilibrium, and product was then filtered off and dried at 50° C. for 17 hours. 1.9 g resulting agglomerates were obtained and had a spherical shape, and the mean particle size ranged from 1.2 mm to 1.6 mm. The average crushing strength of those agglomerates was about 98.2 g/bead.

Example 9

2.0 g of duloxetine HCl was suspended in 300 mL heptane at 20° C. under agitation (paddle, 400 rpm). 4.6 mL of 95% ethanol was added gradually to the suspension. The system was left for 180 min to reach equilibrium, and product was then filtered off and dried at 50° C. for 12 hours. 1.8 g resulting agglomerates were obtained and had a spherical shape, and the mean particle size was about 1.7 mm to 1.9 mm. The average crushing strength of those agglomerates was about 298.8 g/bead.

Example 10

Figure 2A:
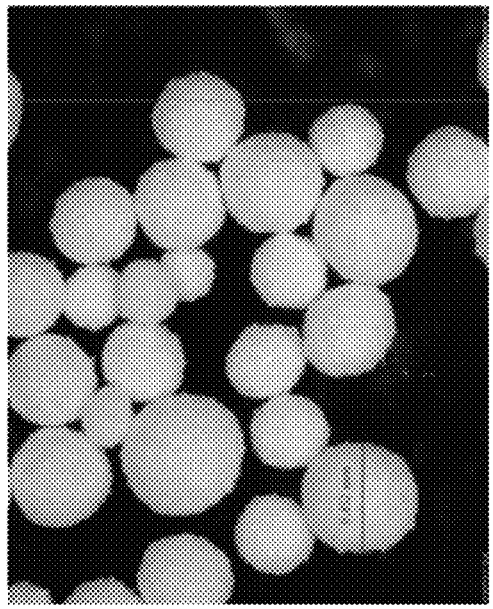
FIGS. 2A-2D are electronic microscopic diagrams illustrating agglomerates containing duloxetine in accordance with an embodiment of the instant disclosure.
Figure 2B:
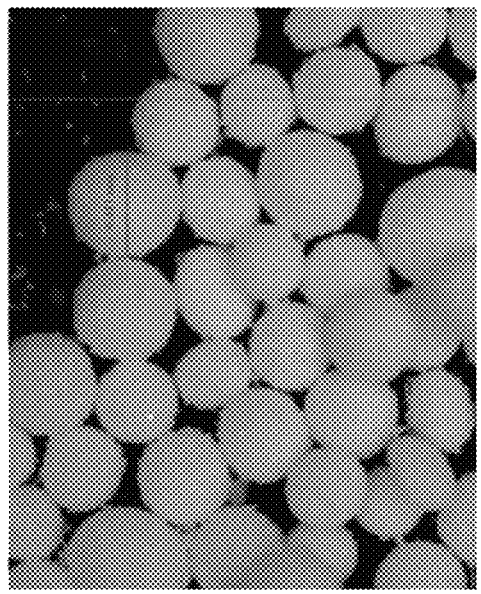
Figure 2C:
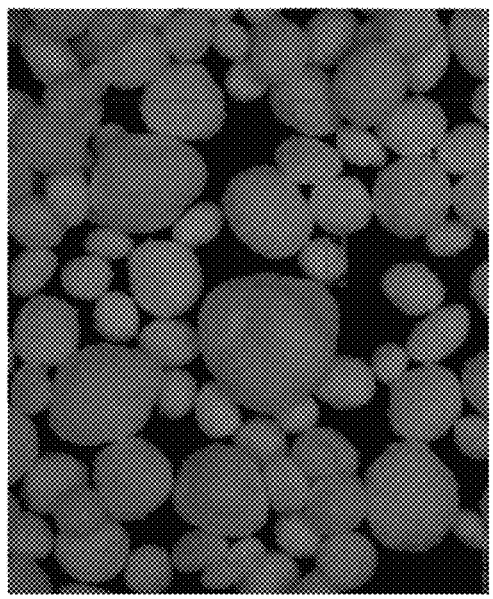
Figure 2D:
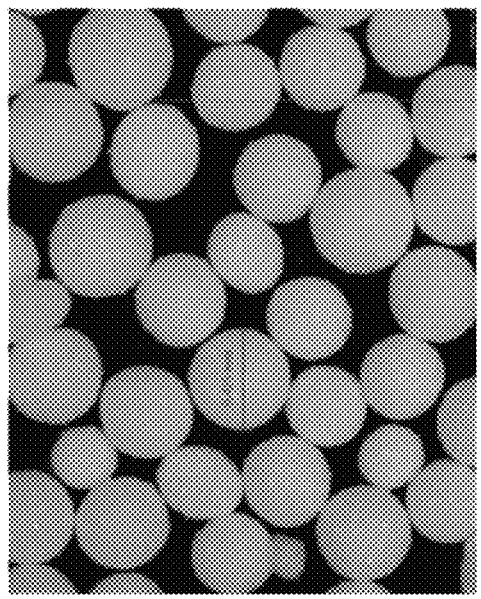

35 g of duloxetine HCl was suspended in 300 mL heptane plus 5 mL acetonitrile at 20° C. under agitation (paddle, 800 rpm). 27 mL of acetonitrile was sprayed by a commercial spray gun (Mod. 951 S 20, from Glatt®) under 20 rpm flow rate and 0.04 bar pressure through a 0.5 mm nozzle to the suspension. The system was left for 180 min to reach equilibrium, and product was then filtered off and dried at 50° C. for 11 hours. 34.7 g resulting agglomerates were obtained and had a spherical shape, and the mean particle size was about 0.3 mm to 0.5 mm. The average crushing strength of those agglomerates was about 43.0 g/beads. FIG. 2 illustrates the agglomerates obtained on different time points after adding acetonitrile during process. FIG. 2A was after 10 min, FIG. 2B was after 40 min, FIG. 2C was after 120 min, and FIG. 2D was after 180 min.

Example 11

Enteric Polymer Coated Duloxetine Pellets

The spherical duloxetine agglomerates obtained from Example 10 were further sealed by a layer containing HPMC and also coated by an enteric layer containing HPMCAS following the steps described in Example 5. The sealing process results in weight gain of about 30.7%, and the enteric layer weight gain was about 7.0%. Each pellet contained about 71.5% w/w of duloxetine HCl. The product was than sieved by #16 and #20 mesh sieves to obtain the particles that were about 0.8 mm to 1.2 mm.

Example 12

Preparation of Cushion Granules and Tablet

The controlled release tablet was made by pressing enteric coated duloxetine pellets and cushion granules.

The cushion granules were prepared by the following steps. 480.0 g of Avicel PH-102 and 30.7 g of PVP K-30 were granulated by adding 150.0 g of purified water in a granulator. The granules were then passed through #16 and #20 mesh sieves.

A mixture was made from 171 g of the cushion granules with 42 g of the enteric duloxetine pellets produced from the Example 11, 57 g of microcrystalline cellulose, 24 g of croscarmellose sodium, 3 g of silicon dioxide and 3 g of glyceryl behenate. The mixture then underwent conventional tablet procedure, and the final tablet weigh was about 300 mg. Each tablet contained about 30 mg of duloxetine HCl.

Example 13

70 g of duloxetine HCl was suspended in 600 mL heptane plus 10 mL acetonitrile at 20° C. under agitation (paddle, 800 rpm). 54 mL of acetonitrile was sprayed by a commercial spray gun (Mod. 951 S 20, from Glatt®) under 20 rpm flow rate and 0.04 bar pressure to the suspension. The system was left for 300 min to reach equilibrium, and product was then filtered off and dried at 50° C. for 11 hours. 69.6 g resulting agglomerates were obtained and had a spherical shape, and the mean particle size was about 0.4 mm. The solvent content of the spherical agglomerates assayed by gas chromatography showed that heptane was 26 ppm, and acetonitrile was not detected.

Example 14

Table 4 shows cushion filling of duloxetine pellets A and duloxetine pellets B, both having modified release rate. The mean particle size of duloxetine pellets A and duloxetine pellets B was approximately 400 μm.

TABLE 4

| | Pellet A (mg/capsule) | Pellet B (mg/capsule) |
|---|---|---|
| Drug Core | | |
| Spherical duloxetine agglomerates (~200 um) | 67.36 | 67.36 |
| Seal Coating | | |
| Methocel E5LV | 4.5 | 4.5 |
| Sucrose | 9 | 9 |
| Micro talc | 13.5 | 13.5 |
| Enteric Layer | | |
| HPMCAS AS-LF | 71.5 | 13.5 |
| TEC | 7.2 | 1.4 |
| Micro talc | 53.6 | — |
| Stearic acid | — | 4.1 |

TABLE 4-continued

| | Pellet A (mg/capsule) | Pellet B (mg/capsule) |
|---|---|---|
| Over Coating | | |
| HPMCAS AS-LF | — | 0.81 |
| TEC | — | 0.08 |
| Stearic acid | — | 0.24 |
| Total | 226.6 | 114.4 |

Example 15

Flowability Comparison

Figure 3B:
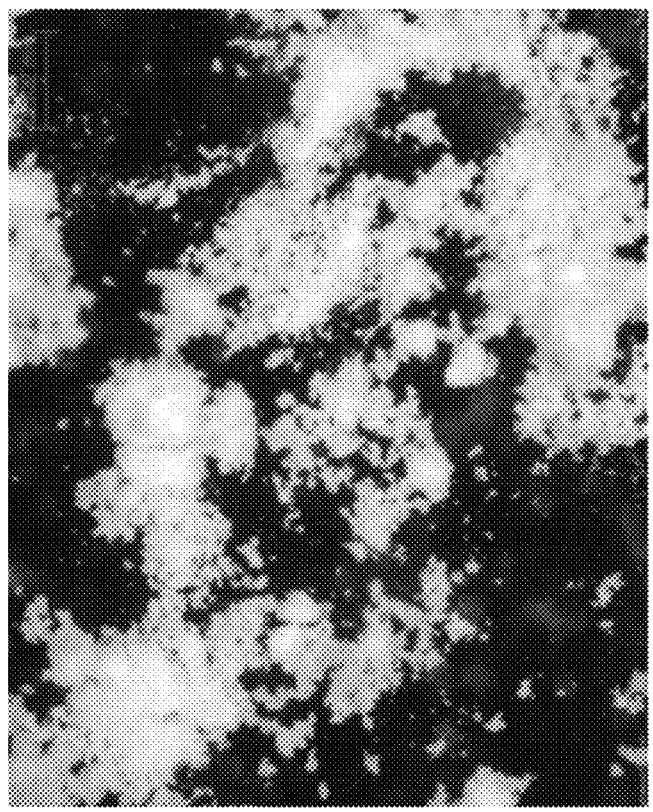
FIGS. 3A-3B are electronic microscopic diagrams illustrating duloxetine in various forms in accordance with an embodiment of the instant disclosure.
Figure 3A:
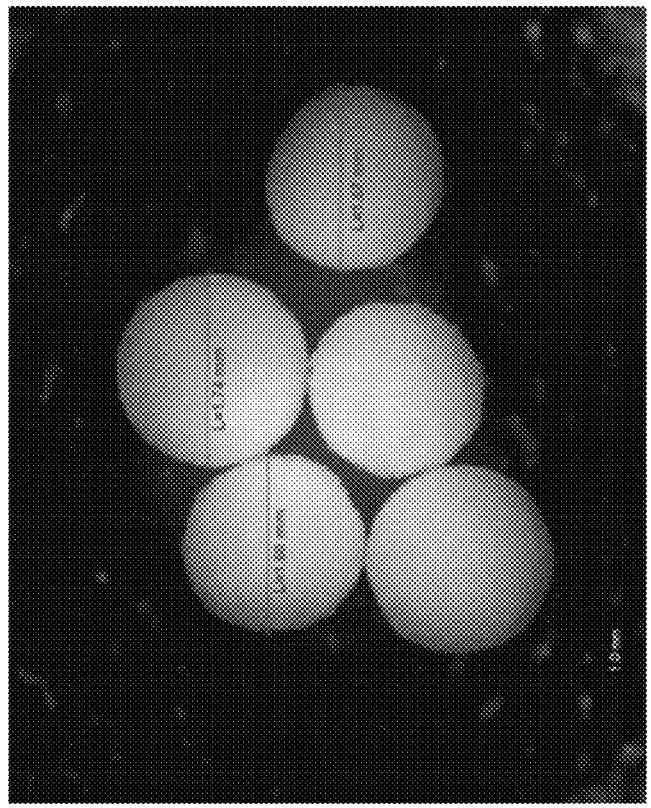

The spherical duloxetine agglomerates, having mean particle size of about 1.6 mm, and crude duloxetine particles were tested for flowability by Carr index. The Carr index of the spherical duloxetine agglomerates is about 8.33%, which was high in flowability. In comparison, the Carr index of the duloxetine crude materials having a mean particle size of about 6.7 μm was about 46.25%, which was low in flowability. FIG. 3 is electronic microscopic diagram. FIG. 3A shows the shape of spherical duloxetine agglomerates made according to the abovementioned process. FIG. 3B shows the duloxetine crude material.

Example 16

Enteric Polymer Coated Duloxetine Pellets

TABLE 5

| | Percentage | Unit Dose (mg) |
|---|---|---|
| Drug Core | | |
| Spherical duloxetine agglomerates (~700 um) | 62.7% | 110.0 |
| Seal Coating | | |
| HPMC | 4.7% | 8.3 |
| Sucrose | 9.4% | 16.5 |
| Micro talc | 14.1% | 24.8 |
| Enteric Layer | | |
| HPMCAS AS-LF | 5.8% | 10.1 |
| TEC | 0.9% | 1.5 |
| Stearic acid | 2.4% | 4.3 |
| Total | 100.0% | 175.5 |

The coated spherical duloxetine agglomerates were assayed for dissolution in a Type I dissolution apparatus according to the U.S. Pharmacopoeia under the condition of firstly 2 hours in an acid medium (0.1N HCl, 1000 mL, basket 100 rpm, 37° C.) and then to a buffer (pH 6.8 PBS, 1000 mL, basket 100 rpm 37° C.). Table 6 shows the release rate result.

TABLE 6

| Time (min) | Release (%) |
|---|---|
| 60 | 0.7 |
| 120 | 6.0 |
| 145 | 45.5 |
| 160 | 62.7 |

TABLE 6-continued

| Time (min) | Release (%) |
|---|---|
| 175 | 67.3 |
| 190 | 79.7 |
| 205 | 83.4 |

Example 17

Different sizes of the spherical duloxetine agglomerates were assayed for compatibility by measuring the residual content (% assay). In comparison, duloxetine crude materials and granulated duloxetine particles having similar size obtained by the conventional wet granulation were also assayed. The granulated duloxetine particles were granulated by the same second solvent (e.g., acetonitrile), which was used in the process of spherical agglomeration, and dried at 50° C. until LOD<1%. An enteric material, hypromellose phthalate (HPMCP) HR-50, which is known to cause degradation of duloxetine, was used in this test.

Figure 4A:
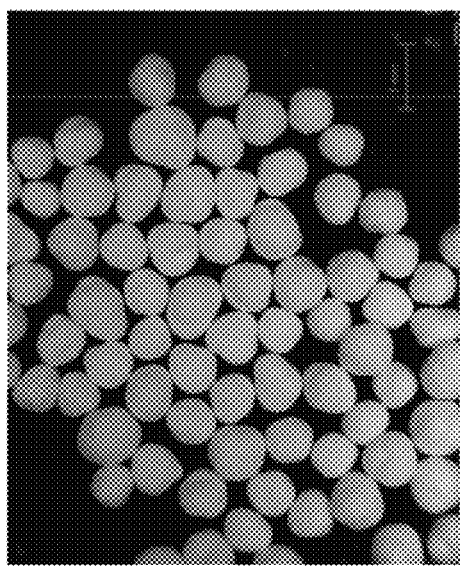
FIGS. 4A-4D are electronic microscopic diagrams illustrating duloxetine in various forms in accordance with an embodiment of the instant disclosure.
Figure 4B:
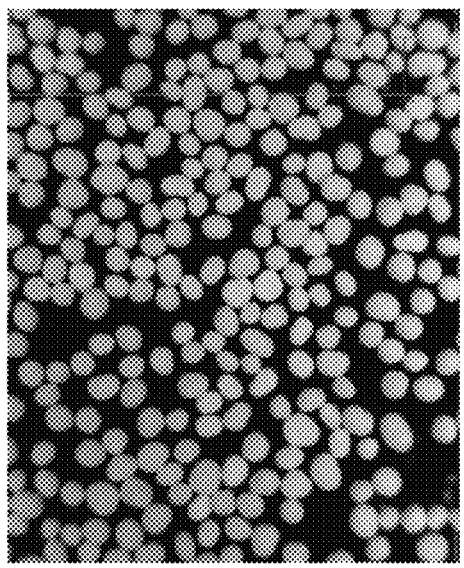
Figure 4C:
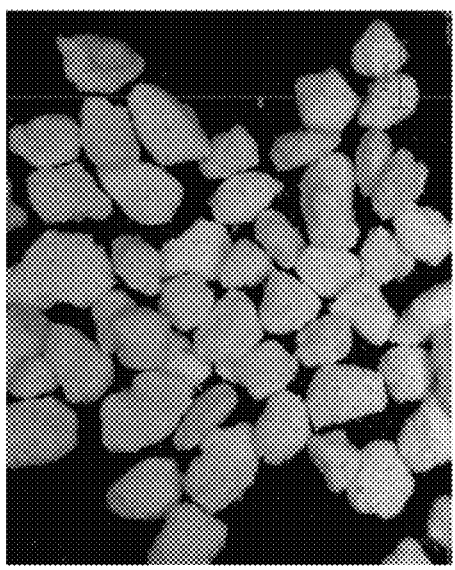
Figure 4D:

According to the result, the spherical agglomerates had a better residual content after a period of storage than the crude materials, which suggested higher compatibility of the agglomerates. In addition, the spherical agglomerates also had a better compatibility than the similar size granulated particles made by conventional granulation, which meant the improved compatibility did not only result from a size enlargement. FIG. 4 is electronic microscopic diagram of duloxetine in different states. FIG. 4A shows the shape of agglomerates under #20-30 mesh. FIG. 4B shows agglomerates under #40-60 mesh. FIG. 4C shows granulated duloxetine particles under #20-30 mesh. FIG. 4D shows granulated duloxetine particles under #40-60 mesh. In Table 7, "C" refers to crude material. "SA" refers to spherical agglomerates. "G" refers to granulated duloxetine particles.

TABLE 7

| Sample ID | Duloxetine:HPMCP | Condition | % Assay |
|---|---|---|---|
| C | 1:0 | 60° C./75% RH, 11 days | 98.39 |
| SA#40-60 | 1:0 | | 98.43 |
| SA#20-30 | 1:0 | | 99.14 |
| G#40-60 | 1:0 | | 98.57 |
| G#20-30 | 1:0 | | 99.19 |
| C + HPMCP | 1:0.6 | | 0.48 |
| SA#40-60 + HPMCP | 1:0.6 | | 95.10 |
| SA#20-30 + HPMCP | 1:0.6 | | 97.66 |
| G#40-60 + HPMCP | 1:0.6 | | 59.91 |
| G#20-30 + HPMCP | 1:0.6 | | 90.31 |

Although the instant disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the instant disclosure without departing from the scope or spirit of the invention. In view of the foregoing, it is intended that the instant disclosure cover modifications and variations of this invention provided they fall within the scope of the following claims.

What is claimed is:

1. A method of preparing drug agglomerates, comprising:
adding a drug powder to a first solvent to form a first solution, wherein the drug powder is suspended;

spraying a second solvent to the first solution to form a second solution, wherein the drug powder undergo nucleation to form drug agglomerates, and the second solvent is immiscible to the first solvent; and isolating drug agglomerates from the second solution.

2. The method of preparing drug agglomerates of claim 1, wherein the first solvent is $C_5$-$C_6$ alkane.

3. The method of preparing drug agglomerates of claim 1, wherein the second solvent is selected from acetonitrile, ethanol, water and the combination thereof.

4. The method of preparing drug agglomerates of claim 1, further comprising:

mixing the first solvent and the second solvent; and adding the drug powder to form the first solution.

5. The method of preparing drug agglomerates of claim 1, wherein the diameter of the droplet of the second solution ranges from 0.1 to 1.0 mm.

6. The method of preparing drug agglomerates of claim 1, wherein the diameter of the drug agglomerate ranges from 0.1 to 2.0 mm, and the drug concentration of the drug agglomerate is equal or higher than 95% (w/w).

7. The method of preparing drug agglomerates of claim 1, wherein the diameter ($d_{90}$) of the drug powder is smaller than 0.05 mm.

8. The method of preparing drug agglomerates of claim 1, wherein the drug powder is an add susceptible drug.

9. The method of preparing drug agglomerates of claim 8, wherein the drug powder is duloxetine.

\* \* \* \* \*